(12) United States Patent
Dugand et al.

(10) Patent No.: US 11,224,694 B2
(45) Date of Patent: Jan. 18, 2022

(54) AUTOMATIC INJECTION DEVICE WITH REDUCED RESIDUAL VOLUME

(71) Applicant: Nemera La Verpillière, La Verpilliere (FR)

(72) Inventors: Pascal Dugand, Estrablin (FR); Kevin Stamp, Sheffield (GB)

(73) Assignee: Nemera La Verpillière

( * ) Notice: Subject to any disclaimer, the term of this patent is extended or adjusted under 35 U.S.C. 154(b) by 327 days.

(21) Appl. No.: 16/318,031

(22) PCT Filed: Jun. 13, 2017

(86) PCT No.: PCT/FR2017/051507
§ 371 (c)(1),
(2) Date: Jan. 15, 2019

(87) PCT Pub. No.: WO2018/011480
PCT Pub. Date: Jan. 18, 2018

(65) Prior Publication Data
US 2020/0238010 A1 Jul. 30, 2020

(30) Foreign Application Priority Data
Jul. 15, 2016 (FR) .................................... 1656809

(51) Int. Cl.
*A61M 5/20* (2006.01)
*A61M 5/315* (2006.01)
(Continued)

(52) U.S. Cl.
CPC ........ *A61M 5/2033* (2013.01); *A61M 5/3153* (2013.01); *A61M 5/31501* (2013.01);
(Continued)

(58) Field of Classification Search
CPC .. A61M 5/20; A61M 5/2033; A61M 5/31501; A61M 5/3153; A61M 5/46;
(Continued)

(56) References Cited

U.S. PATENT DOCUMENTS

| 8,734,394 | B2 * | 5/2014 | Adams | ................ | A61M 5/2033 |
|---|---|---|---|---|---|
| | | | | | 604/135 |
| 8,734,402 | B2 * | 5/2014 | Sharp | .................. | A61M 5/2033 |
| | | | | | 604/198 |
| 2013/0041346 | A1 | 2/2013 | Alon | | |

FOREIGN PATENT DOCUMENTS

| EP | 2047879 A1 | 4/2009 |
|---|---|---|
| FR | 2922455 A1 | 4/2009 |

(Continued)

*Primary Examiner* — Emily L Schmidt
*Assistant Examiner* — Emily J Becker
(74) *Attorney, Agent, or Firm* — St. Onge Steward Johnston & Reens LLC

(57) ABSTRACT

An automatic injection device including an injection syringe equipped with a syringe body and with a piston rod mounted movably in this syringe body so as to cover an injection stroke, a piston control member capable of changing between a configuration in which it is in engagement with the piston rod and a configuration in which it is disengaged from this piston rod, mechanism for moving the piston control member between its two configurations with respect to the piston rod. The mechanism for moving the control member between its two configurations includes a camway carried by a disengagement member and a cam carried by the control member. The disengagement member is movable with respect to the piston rod and the syringe body after the end of the injection stroke, in such a way as to cause the camway to interact with the cam.

15 Claims, 9 Drawing Sheets

(51) Int. Cl.
*A61M 5/46* (2006.01)
*A61M 5/32* (2006.01)
*A61M 5/31* (2006.01)

(52) U.S. Cl.
CPC ............. *A61M 5/46* (2013.01); *A61M 5/3202* (2013.01); *A61M 2005/2086* (2013.01); *A61M 2005/3125* (2013.01)

(58) Field of Classification Search
CPC .. A61M 2005/2086; A61M 2005/3125; A61M 5/31591
See application file for complete search history.

(56) References Cited

FOREIGN PATENT DOCUMENTS

| WO | 03047663 A2 | 6/2003 | |
|---|---|---|---|
| WO | WO 2009/081133 A1 * | 7/2009 | .......... A61M 5/2033 |
| WO | WO 2011/012849 A1 * | 2/2011 | .......... A61M 5/2033 |
| WO | 2015036616 A1 | 3/2015 | |

* cited by examiner

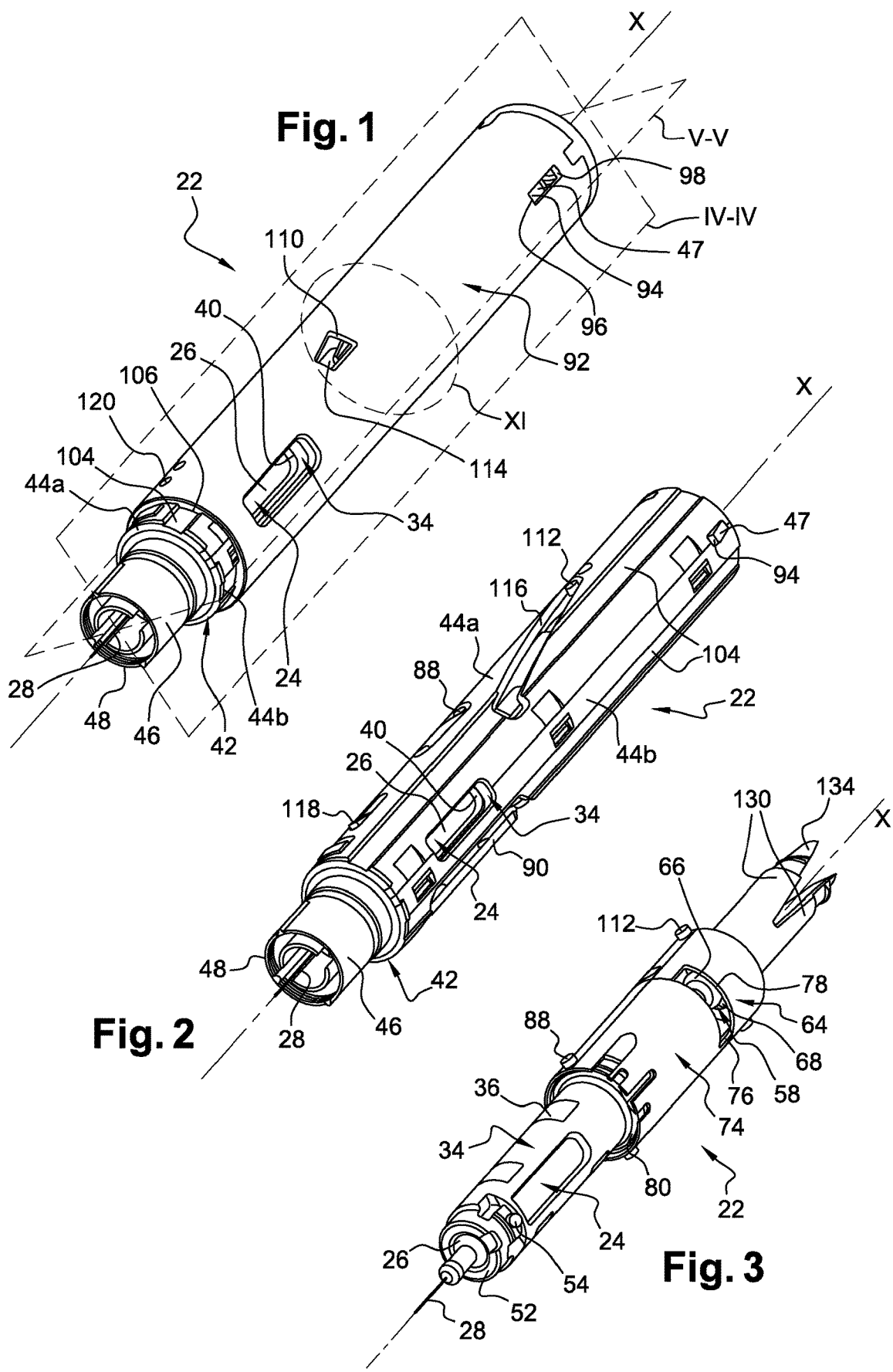

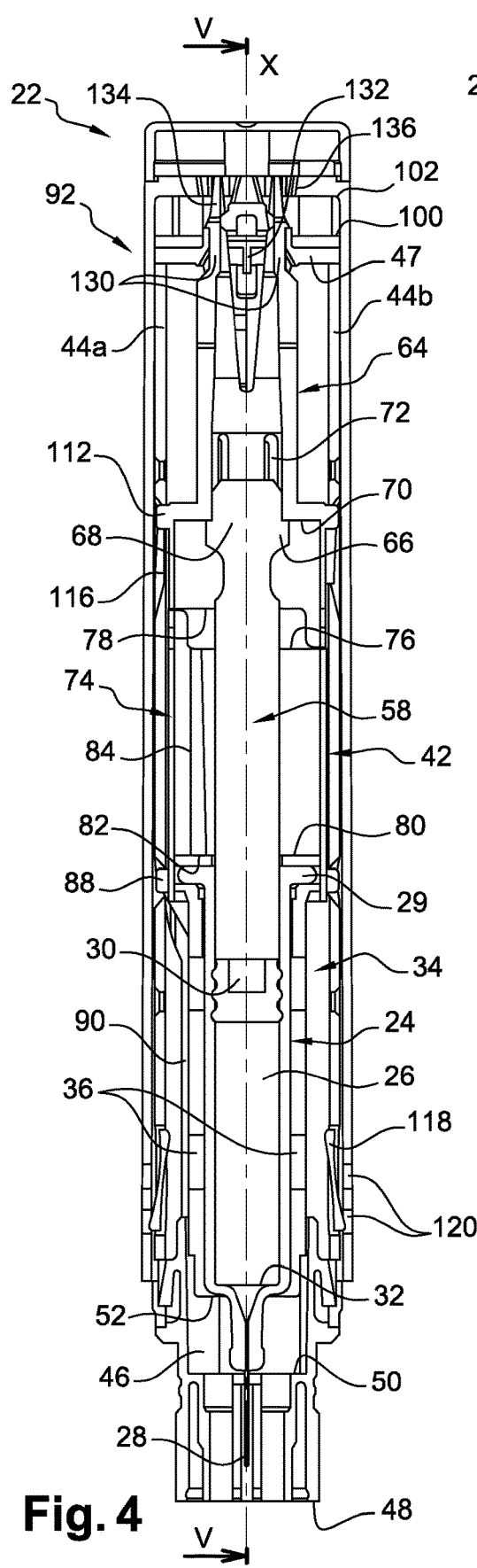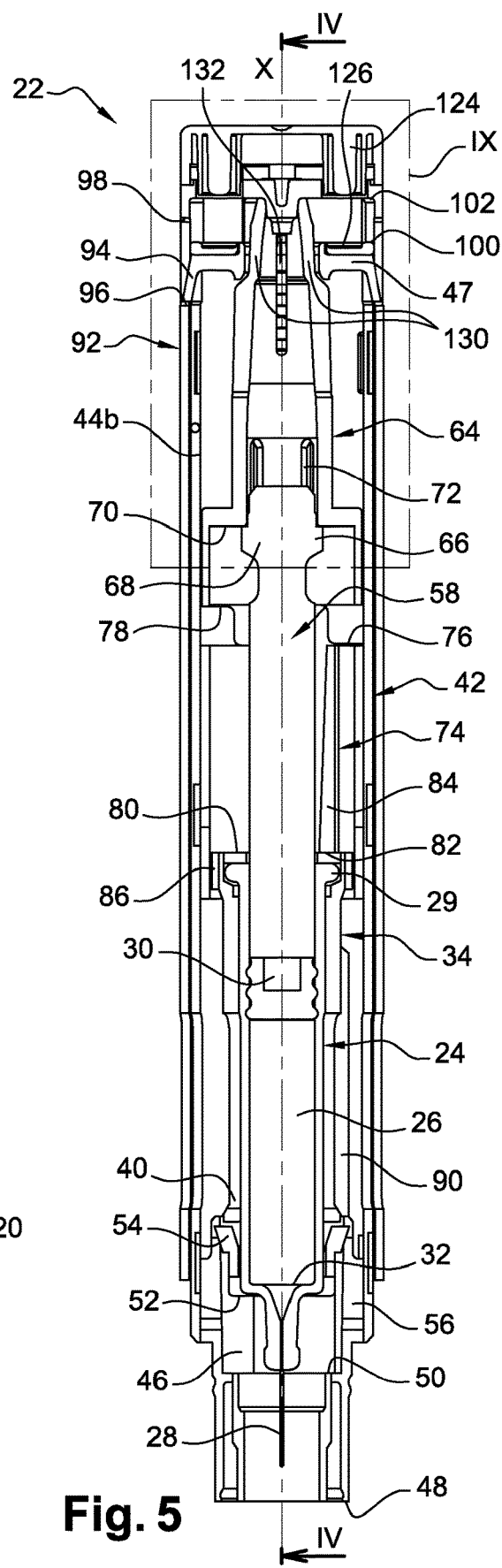
Fig. 4
Fig. 5

AUTOMATIC INJECTION DEVICE WITH REDUCED RESIDUAL VOLUME

FIELD OF THE INVENTION

This invention relates to the field of automatic injection devices for liquid products, especially pharmaceutical.

BACKGROUND OF THE INVENTION

An automatic injection device is used in particular in the medical field, for automatic administration of a liquid medication requiring an injection. Such a device allows in particular a person, for example suffering from rheumatoid arthritis, multiple sclerosis, diabetes or undergoing an anaphylactic shock in case of allergy, to inject themselves a dose of medication independently.

An automatic injection device comprising an injection syringe equipped with a body carrying an injection needle and a piston rod mounted movably in this body to cover an injection stroke whose limit is defined by an abutment of the piston rod in the syringe body is already disclosed in the prior art, in particular in U.S. Pat. No. 8,734,402.

The automatic injection device generally comprises first and second telescopic parts housing the injecting syringe.

The relative displacement of the first and second telescopic parts controls the operation of the automatic injection device.

Thus, to operate the automatic injection device, a user grasps a proximal end of this automatic injection device and presses a distal end of this automatic injection device against the skin to cause a relative movement of the first and second telescopic parts in a direction which shortens the automatic injection device. This automatically causes, in particular due to the triggering of elastic forces, a succession of operating steps, in particular penetration of the injection needle in the user's skin then injection of the liquid product contained in the syringe body through the skin. The injection is followed by a step of retracting the needle inside one of the telescopic parts to avoid any injury.

To perform at least some of these operating steps, the automatic injection device described in U.S. Pat. No. 8,734,402 comprises, firstly, a piston control member, capable of moving between:
  a configuration in which it is engaged with the piston rod to push this piston rod, and
  a configuration in which it is disengaged from this piston rod.

Secondly, the automatic injection device comprises means for moving the control member with respect to the piston rod between its engaged and disengaged configurations.

These means for moving the control member comprise a cam track carried by a positioning control member which, during the injection stroke, is immobilised axially with the syringe body. This cam track cooperates, by relative movement during the injection stroke, with a cam carried by the control member.

We see that the position of the piston rod in the syringe body when the control member reaches its disengaged position is inaccurate due to the dimensional uncertainties of several elements of the automatic injection device. If the piston rod abuts in the syringe body before the control member reaches its disengaged configuration, the control member can no longer move to reach its disengaged configuration. The automatic injection device is then blocked incorrectly and the injection needle does not retract.

To overcome this disadvantage, it is known to adapt the dimensions of the automatic injection device so that the piston rod does not abut in the syringe body before the control member reaches its disengaged configuration. In this case, however, when the control member reaches its disengaged configuration, the liquid contained in the syringe body is not all injected.

SUMMARY OF THE INVENTION

The invention aims in particular to provide an automatic injection device wherein the injection needle is retracted reliably at the end of the injection stroke and wherein the quantity of product not injected is reduced.

This invention therefore relates to an automatic injection device comprising:
  an injection syringe equipped with a syringe body carrying an injection needle and a piston rod mounted movably in this syringe body to cover an injection stroke whose limit is defined by an abutment of the piston rod in the syringe body,
  a piston control member capable of moving between
    a configuration in which it is engaged with the piston rod to push this piston rod, and
    a configuration in which it is disengaged from this piston rod,
  means for moving the piston control member with respect to the piston rod between its engaged and disengaged configurations,
  characterised in that the means for moving the piston control member between its engaged and disengaged configurations comprise at least one first cam track carried by a disengagement member and a cam carried by the piston control member, the disengagement member being movable with respect to the piston rod and the syringe body once the piston rod has reached the end of the injection stroke, in such a way as to cause the first cam track carried by the disengagement member to cooperate with the cam carried by the piston control member.

Thus, when the piston control member moves from the configuration in which it is engaged with the piston rod to the configuration in which it is disengaged, the piston rod can abut in the syringe body before the control member reaches its disengaged configuration, without blocking the operation of the automatic injection device and preventing the retraction of the injection needle. Thus, the disengagement member (which is movable with respect to the piston rod and the syringe body once the piston rod has reached the end of the injection stroke) allows the disengagement member to continue its stroke up to its disengaged configuration by causing the first cam track carried by the disengagement member to cooperate with the cam carried by the control member.

According to other optional characteristics corresponding to different embodiments of the automatic injection device:
  the means for moving the piston control member between its engaged and disengaged configurations further comprise a second cam track carried by a positioning control member which, during the injection stroke, is immobilised axially with the syringe body, this second cam track cooperating, by relative movement during the injection stroke, with the cam carried by the piston control member;
  the disengagement member surrounds at least partially the positioning control member, the disengagement member and the positioning control member comprising means for immobilising their relative rotation equipped with at least one complementary groove and tab;

the tab for immobilising rotation is formed in the disengagement member, the first cam track defining one end of the tab;

the automatic injection device comprises first and second telescopic parts whose relative displacement controls the operation of this automatic injection device, the disengagement member being attached to the first telescopic part, which is intended to be held by a user, and the positioning control member being attached to the second telescopic part;

the disengagement member is made movable with respect to the piston rod and the syringe body once the piston rod has reached the end of the injection stroke by elastic return means acting between the first and second telescopic parts in the direction of an elongation of the automatic injection device;

the elastic return means comprise a plastic spring made integrally with the second telescopic part;

the automatic injection device comprises releasable blocking means for blocking the first and second telescopic parts during at least part of the injection stroke;

the automatic injection device comprises means for releasing the releasable blocking means for blocking the first and second telescopic parts carried by a thrust member attached axially to the piston control member during the injection stroke;

the releasable blocking means comprise at least one retractable ratchet carried by the second telescopic part and cooperating with a notch carried by the first telescopic part;

the means for releasing the releasable blocking means for blocking the first and second telescopic parts comprise a ramp for retracting the retractable ratchet;

the automatic injection device comprises means for limiting the stroke between the first and second telescopic parts;

the means for limiting the stroke comprise a radial projection carried by the second telescopic part cooperating with an edge of a hole formed in the first telescopic part to limit the stroke between the first and second telescopic parts during the elongation of the automatic injection device and two axial stops carried respectively by the first and second telescopic parts arranged so as to limit the stroke between the first and second telescopic parts during the shortening of the automatic injection device;

the automatic injection device comprises visual indication means to indicate the end of the injection stroke;

the visual indication means comprise a window formed through the first telescopic part and at least one visual indicator carried by the piston control member, this visual indicator being positioned opposite the window once the piston rod has reached the end of the injection stroke.

BRIEF DESCRIPTION OF THE DRAWINGS

The invention will be better understood on reading the following description, given solely by way of example and with reference to the accompanying drawings in which:

FIG. 1 is a perspective view of an automatic injection device according to a first embodiment of the invention, in an initial configuration, before the operation of this automatic injection device;

FIG. 2 is a view similar to FIG. 1, the automatic injection device being shown without an outer casing forming a disengagement member;

FIG. 3 is a view similar to FIG. 2, the automatic injection device being shown without a control member;

FIGS. 4 and 5 are sectional views of the automatic injection device respectively along planes IV-IV and V-V of FIG. 1;

DETAILED DESCRIPTION OF THE INVENTION

Figure 6:
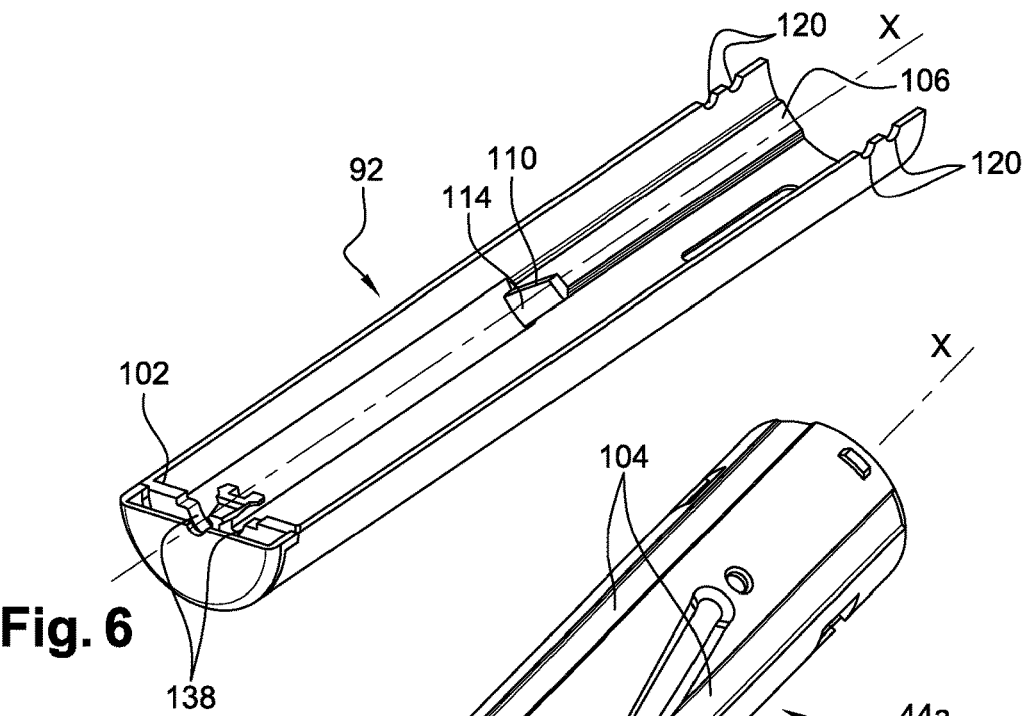
FIG. 6 is a perspective sectional view along the plane IV-IV of the outer casing of the automatic injection device shown on FIG. 1.
Figure 7:
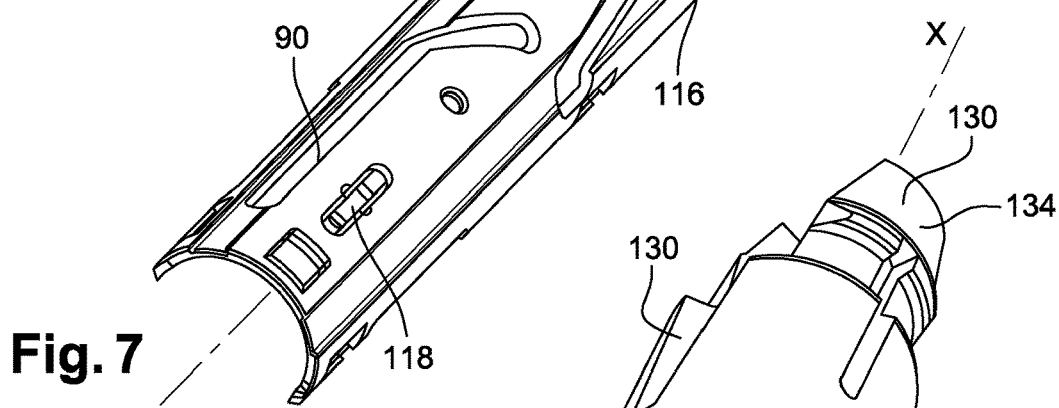
FIG. 7 is a perspective view of a half-shell of the control member of the automatic injection device shown on FIG. 1.

FIGS. 1 to 17 show a device 22 for automatic injection of a liquid product according to a first embodiment of the invention. More precisely, the automatic injection device 22 is a medical device allowing automatic administration of a liquid medication by injection. The automatic injection device 22 has a generally cylindrical shape about an axis X.

The automatic injection device 22 is equipped with an injection syringe 24 (shown in particular on FIGS. 4 and 5) comprising an essentially tubular syringe body 26 of axis X carrying an injection needle 28 at one of its ends. The other end of the syringe body 26 is equipped with a collar 29. A piston 30, of generally cylindrical shape, is mounted slidably in the syringe body 26 for injecting a liquid product contained in the syringe body 26. When the piston 30 moves towards the injection needle 28, it covers an injection stroke during which the liquid contained in the injection syringe 24 is ejected by the ejection needle 28. This stroke is limited by a bottom wall 32 of the syringe body 26 forming a stop for the end of stroke of the piston 30 in the syringe body 26. An initial position of the piston 30 is defined according to the quantity of liquid to be injected. Before assembling the automatic injection device 22, after filling the injection syringe 24, the piston 30 is placed at the initial position. The maximum injection stroke that can be covered by the piston 30 therefore extends from the initial position of the piston 30 up to a limit defined by the abutment of the piston 30 against the bottom wall 32 of the syringe body 26.

In this example, the injection syringe 24 is a prefilled glass cemented needle syringe, of volume 1 mL (millilitre). Note that the syringe body 26 defines a maximum liquid volume, but that it is possible to fill it only partially by placing the piston 30 in a suitable initial position.

To perform an injection, the patient grasps the automatic injection device 22 by one end and presses the other end of this automatic injection device 22 against the skin. A succession of automatically controlled movements of the various members of the automatic injection device 22 then causes insertion of the injection needle 28 into the patient's skin then injection of the content of the syringe body 26 through the injection needle 28. After the injection, the injection needle 28 retracts into the device 22.

In the remainder of the description, the term proximal shall refer to an element of the automatic injection device 22 close to the patient's hand when operating the automatic injection device 22 and the term distal shall refer to an element of the automatic injection device 22 away from the patient's hand. Consequently, the end of the automatic injection device 22 that the patient presses against the skin is a distal end of the automatic injection device 22 and the injection needle 28 is carried by a distal end of the syringe body 26.

When the automatic injection device 22 is not used, it can be equipped with a protective cap (not shown on the figures) of Rigid Needle Shield type (RNS), comprising a soft rubber inner plug intended to receive the end of the injection needle 28 and block it. The inner plug is surrounded by a rigid plastic shell providing the inner plug with good mechanical strength. This protective cap is mounted immobile in a withdrawal member (not shown on the figures) intended to be handled by the user when removing the protective cap. This withdrawal member covers the distal part of the automatic inspection device 22 when it is mounted on the automatic injection device 22.

As shown for example on FIGS. 3 to 5, the injection syringe 24 is positioned inside a syringe support 34 of generally tubular shape of axis X open at both ends. The injection syringe 24 is immobilised inside the syringe support 34 in particular by elastomer elements 36 (shown in particular on FIGS. 13 to 17) connected to the syringe support 34 and in contact with the syringe body 26 so that the injection syringe 24 is immobilised axially by adhesion. Two viewing windows 40 (shown in particular on FIGS. 1 to 2) are formed opposite each other in the syringe support 34. Each viewing window 40 has an elongate shape, extending substantially in the direction of the axis X and allowing the injection syringe 24 to be seen through the syringe support 34.

The syringe support 34 is mounted slidably in a positioning control member 42 of generally tubular shape, of axis X, this positioning control member 42 being substantially longer than the syringe support 34. The positioning control member 42 comprises two half-shells 44a, 44b of generally semi-cylindrical shape, an end sleeve 46 and a retaining bush 47. The various elements 44a, 44b, 46 and 47 of the positioning control member 42 are immobilised with respect to one another. The end sleeve 46 forms the distal part of the positioning control member 42. It is the distal surface 48, the most distal surface of the end sleeve 46, which is intended to be pressed against the patient's skin. The retaining bush 47 has a generally annular shape and is housed in the proximal part of the positioning control member 42. One purpose of the end sleeve 46 is to protect the injection needle 28 against any inadvertent contact with an element of its environment when the automatic injection device 22 is not used. In fact, when the injection needle 28 is inserted in the patient's skin, the injection syringe 24 moves axially with respect to the positioning control member 42 so that the injection needle 28 projects with respect to the distal surface 48 of the end sleeve 46. After the injection, the injection syringe 24 retracts axially into the automatic injection device 22 so that the injection needle 28 no longer projects with respect to the distal surface 48. Thus, before and after operating the automatic injection device 22, the injection needle 28 does not project out of the control member 42.

The syringe support 34 and the positioning control member 42 comprise means for guiding and limiting the stroke between them, comprising in particular:

an inner shoulder 50 of the end sleeve 46 intended to stop the axial movement of the syringe support 34 with respect to the positioning control member 42 in the proximal to distal direction by cooperating with a distal surface 52 of the syringe support 34;

radial lugs 54 (shown in particular on FIG. 5) carried by the syringe support 34 cooperating with axial notches 56 of the end sleeve 46 to prevent the syringe support 34 from rotating about the axis X with respect to the positioning control member 42.

Thus, the only degree of freedom of the syringe support 34 with respect to the positioning control member 42 is translation along the axis X.

The injection syringe 24 comprises a piston rod 58 kinematically connected to the axial movement of the piston 30, and therefore displaceable in the syringe body 26. The piston rod 58 has a generally cylindrical shape of axis X. The distal end of the piston rod 58 cooperates axially with the proximal end of the piston 30. As an alternative, the piston rod 58 and the piston 30 can be screwed to each other. Since the piston rod 58 and the piston 30 are kinematically connected in their axial movement, these two members cover the injection stroke jointly.

Figure 8:
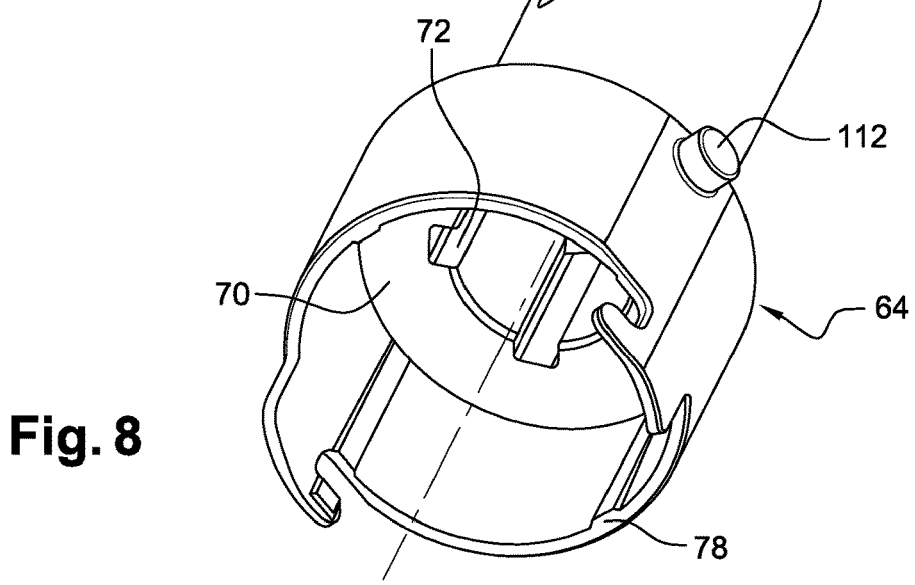
FIG. 8 is a perspective view of a piston control member of the automatic injection device shown on FIG. 1.

FIG. 8 shows a piston control member 64 of generally tubular shape of axis X. The piston control member 64 is mounted slidably in the positioning control member 42. The piston control member 64 cooperates with the proximal part of the piston rod 58 so that the piston control member 64 can move angularly with respect to the piston rod 58 between:

a configuration in which it is engaged with the piston rod 58 to push this piston rod 58, and a configuration in which it is disengaged from this piston rod 58.

The piston rod 58 is equipped at its proximal end with a proximal shoulder 66 on which four radial projections 68 are formed. The piston control member 64 is equipped with an inner shoulder 70 in which four axial grooves 72 are formed. The outer contour defined by the proximal shoulder 66 and the four radial projections 68 of the piston rod 58 has a shape which is complementary to the inner contour defined by the inner shoulder 70 and the four grooves 72 of the piston control member 64. Thus, when the four radial projections 68 are shifted angularly with respect to the four axial grooves 72, the piston control member 64 is in the configuration in which it is engaged with the piston rod 58. In the configuration in which it is engaged with the piston 58, the four radial projections 68 cooperate with the inner shoulder 70 and the piston control member 64 can push the piston 30 towards the distal end of the positioning control member 42. When the four radial projections 68 and the four axial grooves 72 are opposite one another, as shown on FIG. 10, the piston control member 64 is in a disengaged configuration. In the disengaged configuration, the radial projections 68 can engage in the axial grooves 72. When the piston control member 64 and the piston rod 58 move towards each other axially, the piston rod 58 can retract into the piston control member 64.

The automatic injection device 22 further comprises a needle control member 74 of generally tubular shape. The needle control member 74 is mounted slidably in the positioning control member 42. The proximal part of the needle control member 74 is equipped with a proximal surface 76 cooperating axially with a distal surface 78 of the distal part of the piston control member 64. Thus, the needle control member 74 and the piston control member 64 are kinematically connected in their axial movements. The needle control member 74 cooperates with the proximal part of the syringe support 34 so that the needle control member 74 can move angularly with respect to the syringe support 34 between:

a configuration in which it is engaged with the syringe support 34 to push this syringe support 34 and a configuration in which it is disengaged from this syringe support 34.

Figure 13:
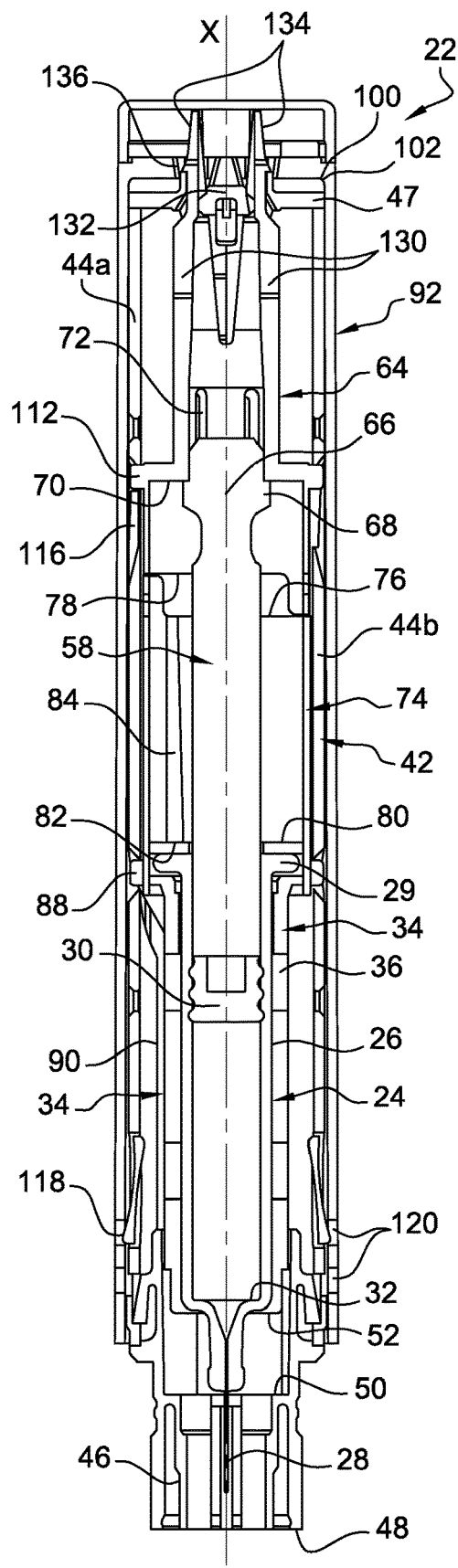
FIGS. 13 to 17 are sectional views along the plane IV-IV of the automatic injection device shown on FIG. 1, in various operating configurations of the automatic injection device.
Figure 14:
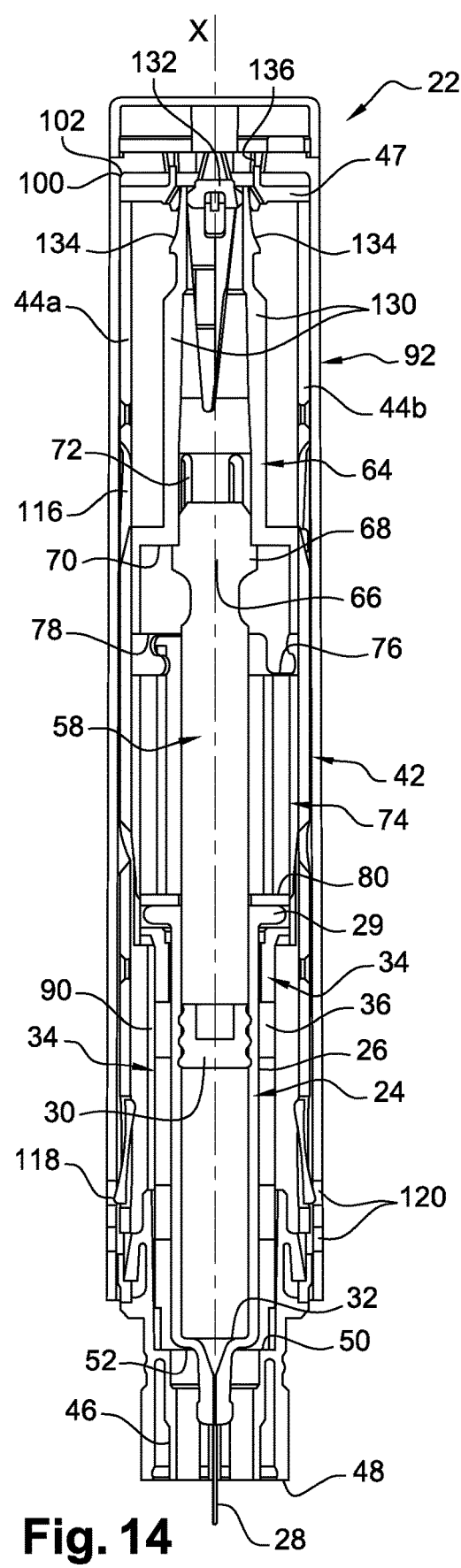
Figure 15:
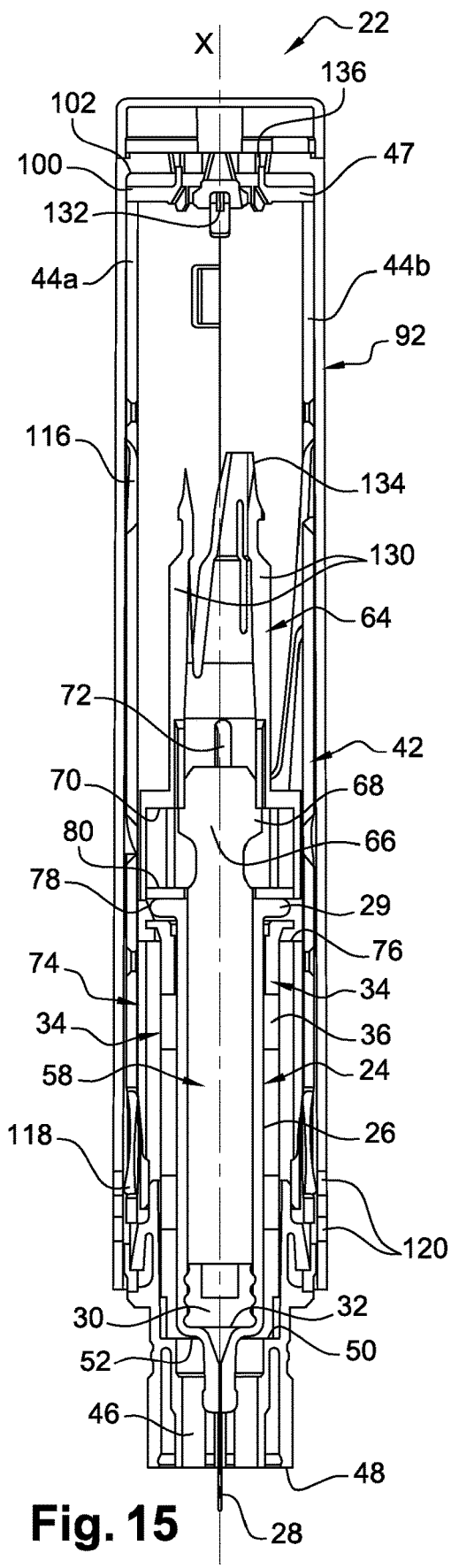
Figure 16:
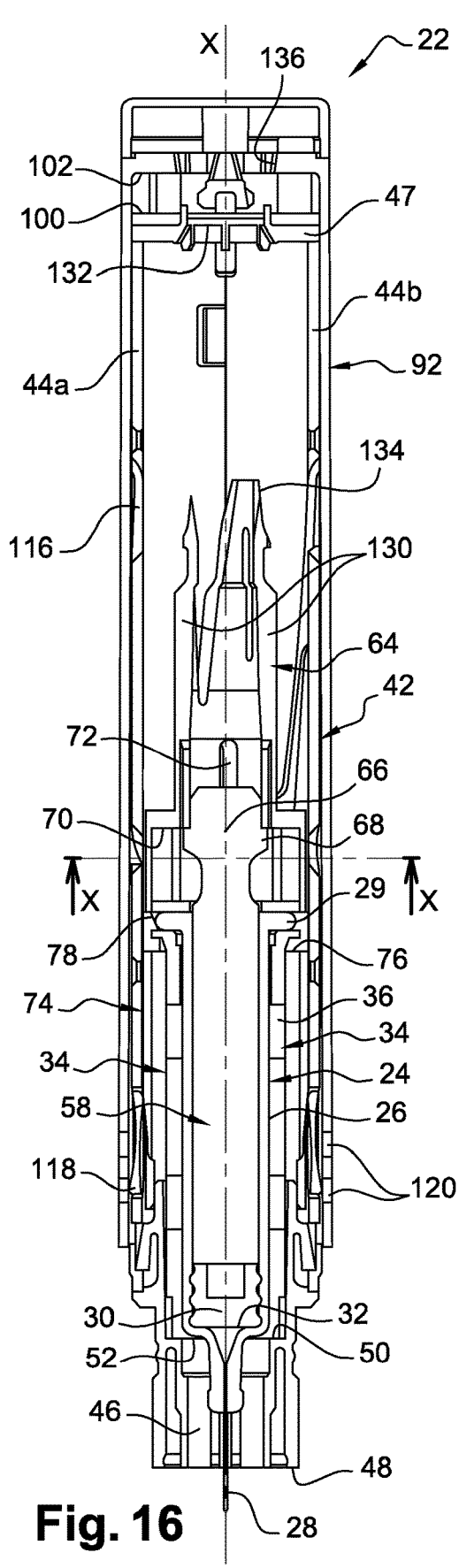
Figure 17:
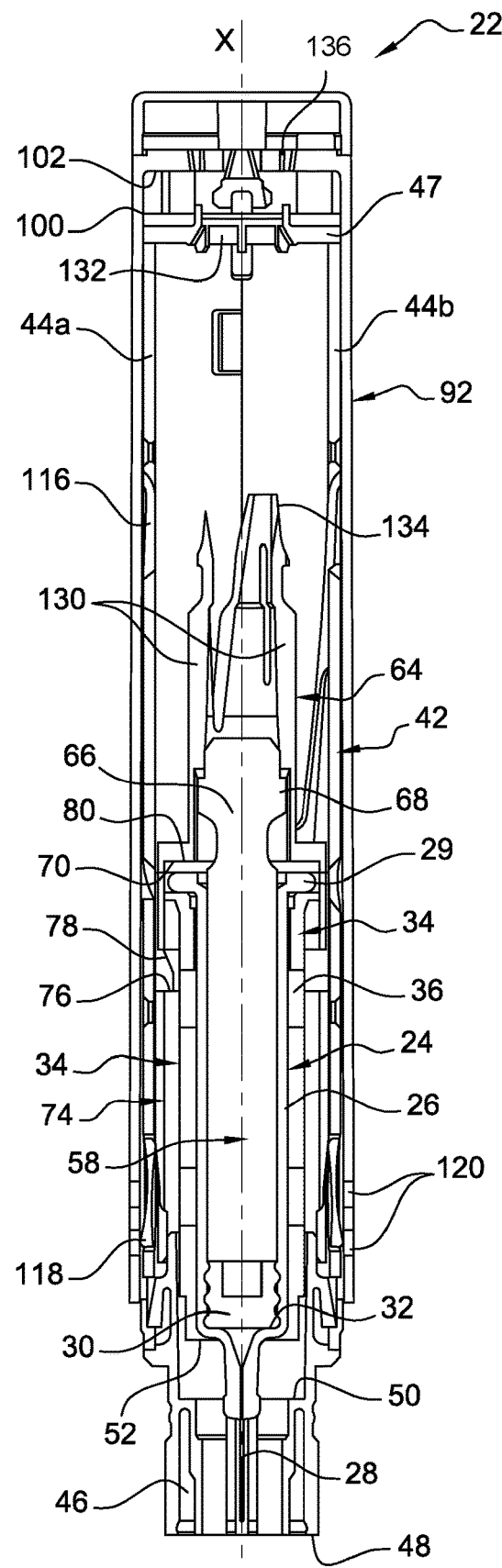
Figure 18:
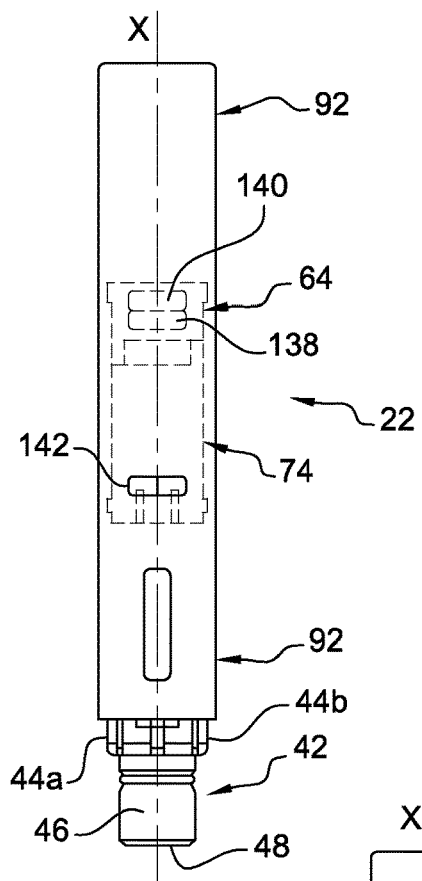
FIGS. 18 to 21 are front views of an automatic injection device according to a second embodiment of the invention comprising visual indication means to indicate the end of the injection stroke in various configurations.
Figure 19:
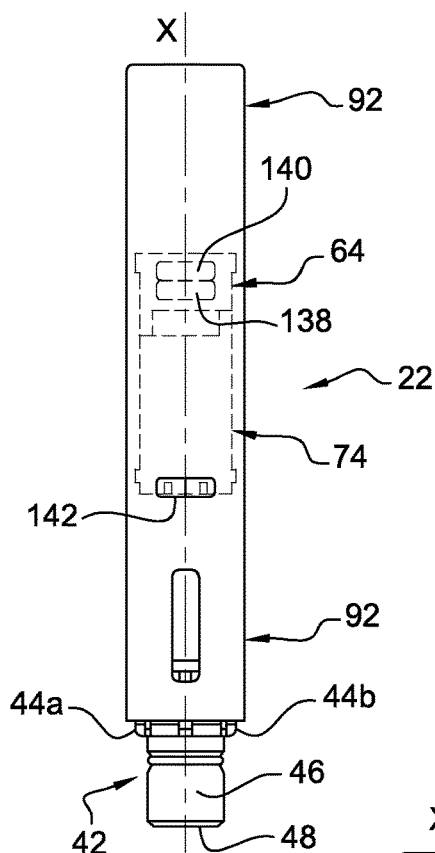

As illustrated in particular on FIGS. 4, 5 and 13, the syringe support 34 is equipped at its proximal end with a contact surface 80 which can cooperate with two surfaces forming an axial stop 82 which are carried by two inner radial projections 84 of the needle control member 74. Two grooves 86 are formed in the contact surface 80 of the syringe support 34. When these grooves 86 are aligned with the axial stops 82 of the needle control member 74, they allow these axial stops 82 to cross the contact surface 80 of the syringe support 34. Thus, when the inner radial projections 84 of the needle control member 74 are shifted angularly with respect to the grooves 86 of the syringe support 34, the needle control member 74 is in the configuration in which it is engaged with the syringe support 34 to push this syringe support 34. In this configuration, the axial stops 82 cooperate with the contact surface 80 of the syringe support 34 and the needle control member 74 can push the syringe support 34 towards the distal end of the positioning control member 42. When the inner radial projections 84 of the needle control member 74 are aligned with the grooves 86 of the syringe support 34, the needle control member 74 is in a configuration in which it is disengaged from the syringe support 34. In the disengaged configuration, the inner radial projections 84 can engage in the grooves 86. When the needle control member 74 and the syringe support 34 move towards each other axially, the needle control member 74 can move forward around the syringe support 34 without pushing it.

The needle control member 74 is equipped with a cam 88 cooperating with a needle control cam track 90 formed in the positioning control member 42. This needle control cam track 90 is intended to turn the needle control member 74 so that when the syringe support 34, pushed by the needle control member 74, reaches the end of its axial movement for inserting the injection needle 28, the needle control member 74 reaches, by rotation, the configuration in which it is disengaged from the syringe support 34.

Note that the automatic injection device 22 comprises first and second telescopic parts whose relative displacement controls the operation of this automatic injection device 22. The positioning control member 42 forms, in fact, the second telescopic part mounted slidably in an outer casing 92 forming the first telescopic part. The outer casing 92 partially surrounds the positioning control member 42 and is intended to be held by the user. The outer casing 92 has a generally tubular shape of axis X partially closed at its proximal end. When the outer casing 92 moves towards the proximal part of the control member 42, the total length of the automatic injection device 22 increases. This displacement direction is referred to as the elongation direction of the automatic injection device 22. On the contrary, when the outer casing 92 moves towards the distal part of the positioning control member 42, the total length of the automatic injection device 22 decreases. This displacement direction is referred to as the shortening direction of the automatic injection device 22. Means for limiting the stroke between the outer casing 92 and the positioning control member 42 comprise:

two radial projections 94 carried by the retaining bush 47 of the positioning control member 42 intended to cooperate with edges 96 of holes 98 (shown in particular on FIG. 1) formed in the outer casing 92 to limit the stroke of the positioning control member 42 during the elongation of the automatic injection device 22;

two axial stops 100, 102 carried respectively by the positioning control member 42 and the outer casing 92, arranged so as to limit the stroke between the positioning control member 42 and the outer casing 92 during the shortening of the automatic injection device 22;

grooves 104 (shown on FIGS. 2 and 7) formed in the positioning control member 42 and tabs 106 carried by the inner surface of the outer casing 92 cooperating so as to prevent the outer casing 92 from rotating with respect to the positioning control member 42.

The outer casing 92 forms a disengagement member 92 carrying a first cam track 110 intended to cooperate with a cam 112 carried by the piston control member 64. This first cam track 110 is formed by the edge 110 of a window 114 which defines the end of one of the tabs 106. The first cam track 110 and the cam 112 of the piston control member 64 form means for displacing the piston control member 64 with respect to the piston rod 58 between its engaged and disengaged configurations. The first cam track 110 is inclined with respect to the axis X so that when the first cam track 110 and the cam 112 of the piston control member 64 cooperate and when the piston control member 64 moves towards the distal part of the disengagement member 92, the piston control member 64 turns with respect to the piston rod 58.

A second cam track 116 is formed in the positioning control member 42. Like the first cam track 110, this second cam track 116 is inclined with respect to the axis X so that when the second cam track 116 and the cam 112 of the piston control member 64 cooperate and when the piston control member 64 moves towards the distal part of the positioning control member 42, the piston control member 64 turns with respect to the piston rod 58. The inclination and position of this second cam track 116 are such that when the piston 30 and the piston rod 28 abut against the bottom wall 32 of the injection syringe 24, the piston control member 64 does not reach its disengagement configuration by cooperating with the second cam track 116. For the piston control member 64 to reach its disengagement configuration, the first cam track 110 must cooperate with the piston control member 64 to drive it to its disengagement configuration. This cooperation between the first cam track 110 and the piston control member 64 occurs after the end of the injection, in other words once the piston 30 and the piston rod 58 have reached the end of the injection stroke.

The positioning control member 42 is equipped with releasable blocking means for blocking the positioning control member 42 and the outer casing 92, during at least part of the injection stroke. These releasable blocking means comprise two retractable ratchets 118 (shown in particular on FIGS. 13 to 17), positioned each side of the positioning control member 42 on each of the two half-shells 44a and 44b, intended to cooperate with four notches 120 consisting of four holes 120 formed in the outer casing 92. The four holes 120 are grouped in twos so that each retractable ratchet 118 can cooperate with two notches 120. Two notches 120 cooperating with the same retractable ratchet 118 are aligned in the direction of the axis X. The retractable ratchets 118 are formed by rockers pivoting between:
- a release configuration, in which the distal end of the retractable ratchets 118 does not project with respect to the positioning control member 42, and
- a blocking configuration in which the distal end of the retractable ratchets 118 projects towards the outside of the positioning control member 42 and a proximal end of the retractable ratchets 118 projects towards the inside of the positioning control member 42.

When they are in their blocking configuration, the retractable ratchets 118 can cooperate with the notches 120. When a retractable ratchet 118 cooperates with a notch 120, the positioning control member 42 cannot move towards the distal end of the outer casing 92 with respect to this outer casing 92 but can nevertheless move in the opposite direction. The automatic injection device 22 further comprises means for releasing the releasable blocking means 118, 120 carried by a thrust member. This thrust member consists of the needle control member 74. The thrust member comprises a retractable ramp adapted to cooperate with the proximal end of the retractable ratchets 118 so that the retractable ratchets 118 are locked in their release position. The needle control member 74 cooperates axially with the ratchets 118, during the axial movement of the needle control member 74 in the positioning control member 42. When the needle control member 74 does not cooperate with the retractable ratchets 118, the retractable ratchets 118 are not locked in their release position and are returned elastically to their blocking position.

The automatic injection device 22 is equipped with elastic return means acting between the outer casing 92 and the positioning control member 42. These elastic return means comprise two return springs 122, shown only on FIG. 9, positioned between spring supports 124 of the outer casing 92 and bearing surfaces 126 of the positioning control member 42. The return springs 122 are metallic compression springs 122 acting in the direction of elongation of the automatic injection device 22. The spring supports 124 are axial protuberances located inside the proximal part of the outer casing 92. The bearing surfaces 126 of the positioning control member 42 are distal surfaces of the positioning control member 42. As an alternative, these metallic springs 122 can be replaced by plastic springs made integrally with the positioning control member 42.

Figure 9:
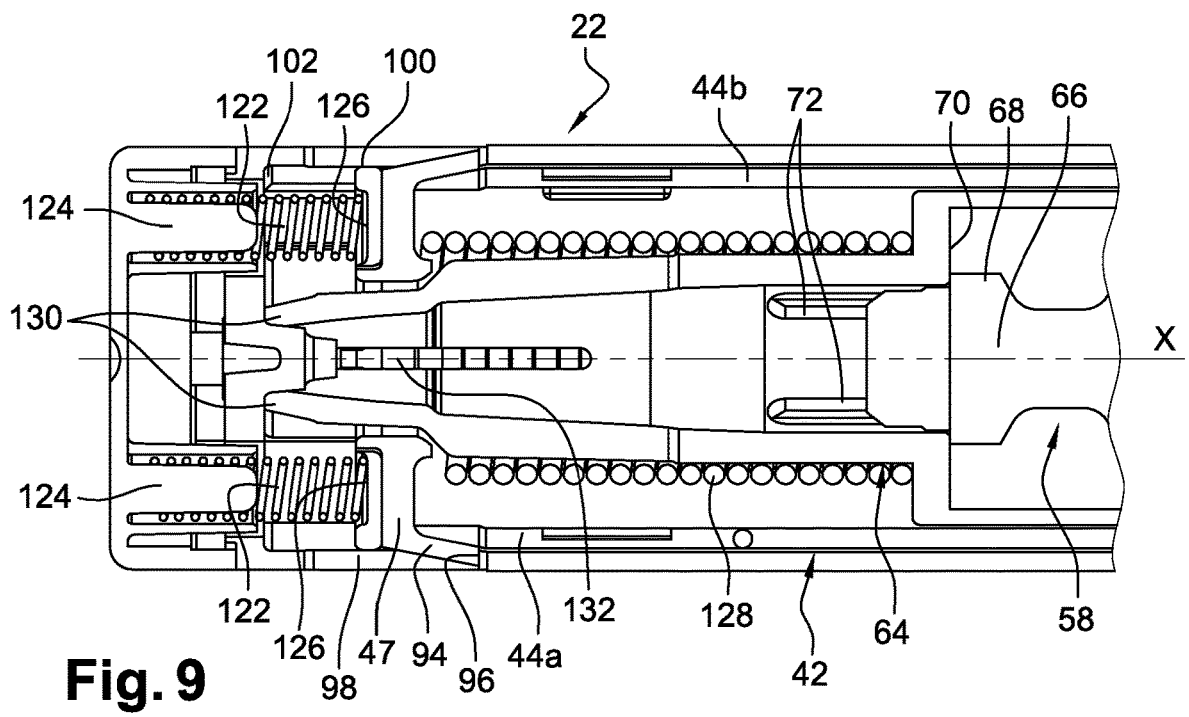
FIG. 9 is a detail view of the circled part IX of the automatic injection device of FIG. 5 showing injection springs no shown on FIG. 5.
Figure 10:
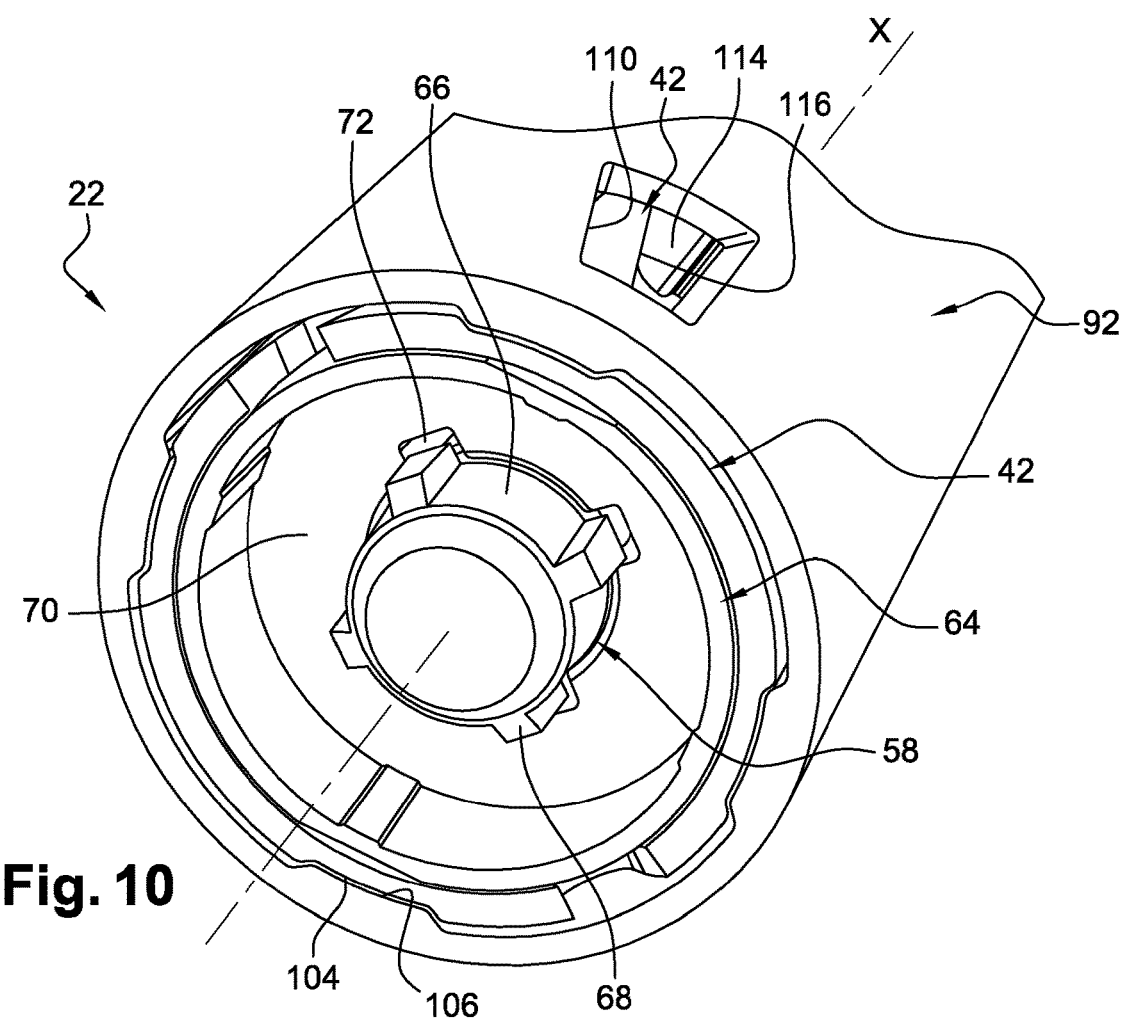
FIG. 10 is a perspective sectional view along a plane X-X of FIG. 16, of the automatic injection device shown on FIG. 1, in which the piston control member is in a disengaged configuration.
Figure 11:
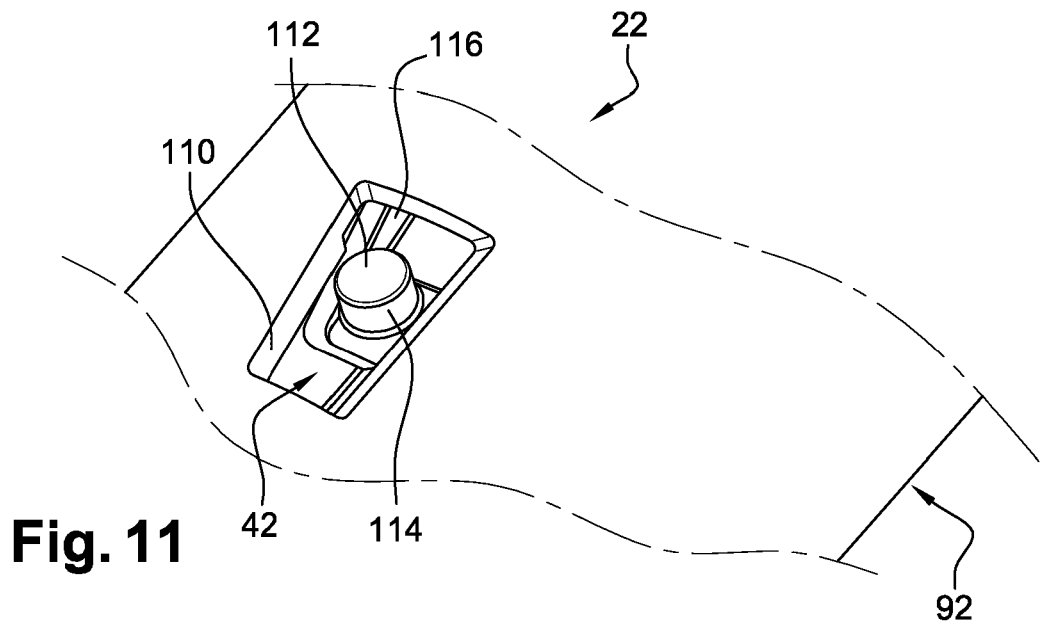
FIGS. 11 and 12 are detailed views of the circled part XI of FIG. 1, in various operating configurations of the automatic injection device.
Figure 12:
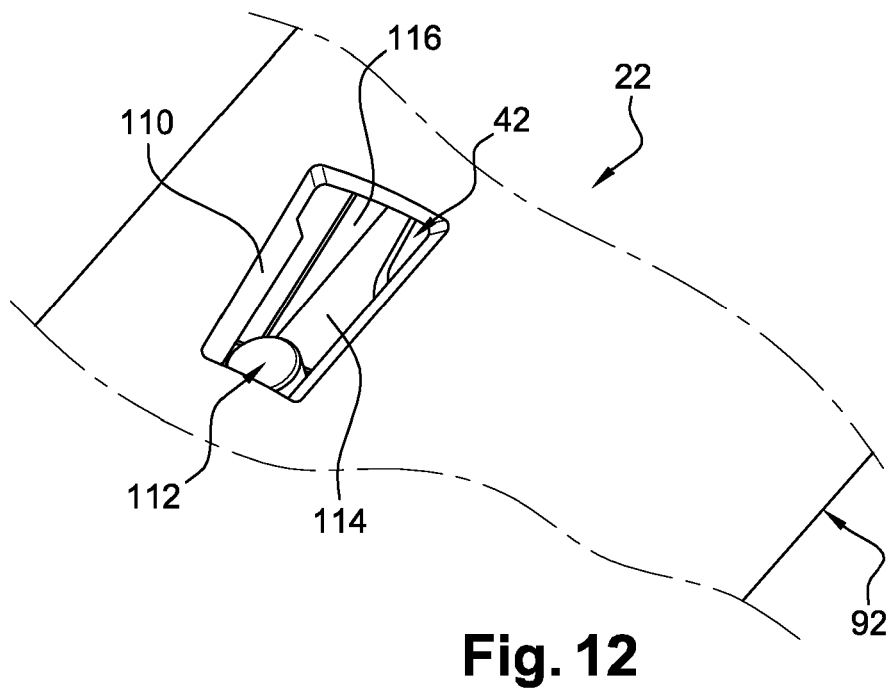

An injection spring 128, shown only on FIG. 9, is positioned in the proximal end of the positioning control member 42. The injection spring 128 acts axially between the positioning control member 42 and the piston control member 64, so as to push the piston control member 64 towards the distal part of the positioning control member 42. The piston control member 64 carries at its proximal end two release tabs 130 for releasing the injection spring 128. The release tabs 130 are intended to cooperate with a hole 132 in the retaining bush 47 so as to axially immobilise the positioning control member 42 and the piston control member 64. The release tabs 130 are equipped with ramps 134 (shown only on FIG. 8) adapted to cooperate with release surfaces 136 of the outer casing 92.

A retraction spring (not shown on the figures) is positioned between the end sleeve 46 and the syringe support 34. The retraction spring is a compression spring with one end resting on an inner shoulder 138 of the end sleeve 46 and the other end resting on a shoulder 140 of the syringe support 34. This retraction spring pushes the syringe support 34 in the direction of the movement which retracts the syringe support 34 into the positioning control member 42. This retraction movement is a movement of the syringe support 34 towards the proximal end of the positioning control member 42.

The various operating steps of the automatic injection device 22 will be described below.

To operate the automatic injection device 22, the withdrawal member and the protective cap of the distal part of the automatic injection device 22 must first be removed. The automatic injection device 22 is then in the configuration shown on FIG. 1, which will be referred to as the initial configuration. The user then grasps the automatic injection device 22 by the outer casing 92 and presses the distal surface 48 of the end sleeve 46 against the skin at the position where the liquid contained in the syringe body 26 is to be injected.

Then, during an unlocking step, the user applies an axial force, towards the distal part of the automatic injection device 22, on the outer casing 92. Thus, the outer casing 92 moves axially towards the distal part of the positioning control member 42. This displacement causes the ramps 134 of the release tabs 130 to cooperate with the release surfaces 136 of the outer casing 92. The release tabs 136 are then deformed towards the inside and no longer axially immobilise the piston control member 64 with the positioning control member 42. During this step, the retractable ratchets 118 move from a configuration in which they cooperate with the two most distal notches 120 of the outer casing 92 to a configuration in which they cooperate with the two most proximal retractable ratchets 118 of the outer casing 92. The outer casing 92 is then immobilised in the direction of elongation of the automatic injection device 22. The automatic injection device 22 then reaches the configuration shown on FIG. 13, in which the piston control member 64 is free to move axially towards the distal part of the positioning control member 42, and the two axial stops 100 and 102 carried by the positioning control member 42 and the outer casing 92 cooperate.

An insertion step occurs after this unlocking step. The injection spring 128 pushes axially the needle control member 74 and the piston control member 64 towards the distal part of the positioning control member 42. Since the needle control member 74 is in the configuration in which it is engaged with the syringe support 34, it cooperates axially with the syringe support 34 and moves the latter so that the injection needle 28 now projects with respect to the distal surface 48 of the end sleeve 46 and is inserted in the patient's skin. During this step, the cam 88 of the needle control member 74 cooperates with the needle control cam track 90 so that the needle control member 74 turns with respect to the syringe support 34 up to the configuration in which it is disengaged from the syringe support 34. Similarly, the cam 112 of the piston control member 64 cooperates with the second cam track 116 so that the piston control member 64 turns with respect to the piston rod 58. However, the piston control member 64 does not reach the configuration in which it is disengaged from the piston rod 58. After this step, the automatic injection device 22 is in the configuration shown on FIG. 14, in which the piston control member 64 is in the configuration in which it is engaged with the piston rod 58, the needle control member 74 is in its disengaged configuration and the inner shoulder 50 of the end sleeve 46 cooperates with the distal surface 52 of the syringe support 34. In this configuration, the injection needle 28 is inserted in the patient's skin.

An injection step occurs after this insertion step. The injection spring 128 continue to push axially the needle control member 74 and the piston control member 64 towards the distal part of the positioning control member 42, however, the needle control member 74 no longer cooperates axially with the syringe support 34. Since the piston control member 64 is in the configuration in which it is engaged with the piston rod 58, it cooperates axially with the piston rod 58 and pushes the latter so that it covers its injection stroke. The pharmaceutical liquid is then injected into the patient's body. During this step, the cam 112 of the piston control member 64 continues to cooperate with the second cam track 116, by relative movement, but does not reach the configuration in which it is disengaged from the piston rod 58. During this step, the needle control member 74 cooperates with the proximal end of the retractable ratchets 118 and locks them in their release configuration. When the retractable ratchets 118 are in release configuration, the outer casing 92 can again move axially towards the distal end of the positioning control member 42. After this step, the automatic injection device 22 is in the configuration shown on FIG. 15, in which the piston 30 and the piston rod 58 abut against the bottom wall 32 of the syringe body 26, the piston control member 64 is in the configuration in which it is engaged with the piston rod 58 and the retractable ratchets 118 of the positioning control member 42 are in release configuration.

A retraction triggering step occurs after this injection step. To trigger the retraction of the injection needle 28, the first cam track 110, carried by the outer casing 92, must cooperate with the cam 112 of the piston control member 64. To allow this cooperation, the user must release the axial force applied on the outer casing 92 so that the return spring 122 can move the outer casing 92 in the direction of elongation of the automatic injection device 22. Note that during this step, the disengagement member 92 is movable with respect to the piston rod 58 and the syringe body 26. During this displacement, the first cam track 110 cooperates with the cam 112 of the piston control member 64 which drives in rotation the piston control member 64 with respect to the piston rod 58 up to the configuration in which it is disengaged from the piston rod 58. After this step, the automatic injection device 22 is in the configuration shown on FIG. 16, in which the piston control member 64 is in the configuration in which it is disengaged from the piston rod 58, and the radial projections 94 of the retaining bush 47 cooperate with the edges 96 of the holes 98 formed in the outer casing 92.

A retraction step occurs after this retraction triggering step. Since the piston control member 64 is in the configuration in which it is disengaged from the piston rod 58, the latter is free to move axially towards the proximal part of the automatic injection device 22. This retraction spring is then free to push the syringe support 34 towards the proximal part of the positioning control member 42. Thus, the injection needle 28 retracts into the positioning control member 42 so that it no longer projects past the distal surface of the end sleeve 46. After this step, the automatic injection device 22 is in the configuration shown on FIG. 17, in which the injection needle 28 does not project out of the positioning control member 42. When the automatic injection device 22 is in this configuration, its operation is finished. The patient can then move the automatic injection device 22 away from the skin.

We will now describe, referring to FIGS. 18 to 21, an automatic injection device 22 according to a second embodiment of the invention. In this case, the elements similar to those of the preceding figures are designated by the same references.

Figure 20:
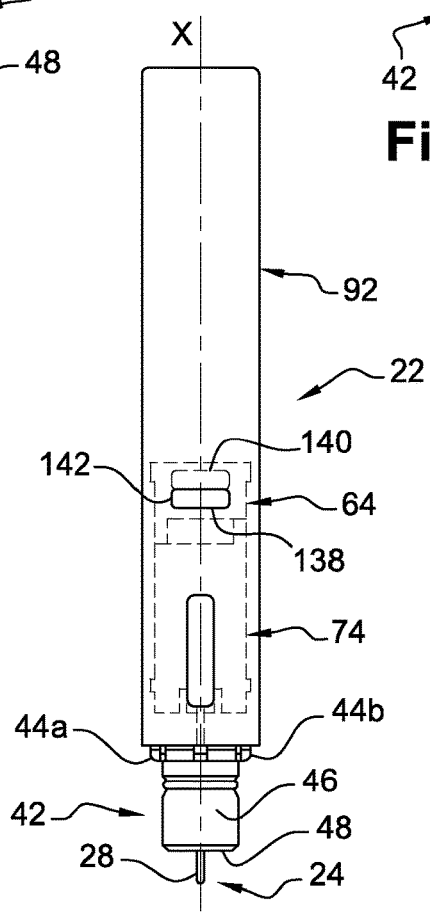
Figure 21:
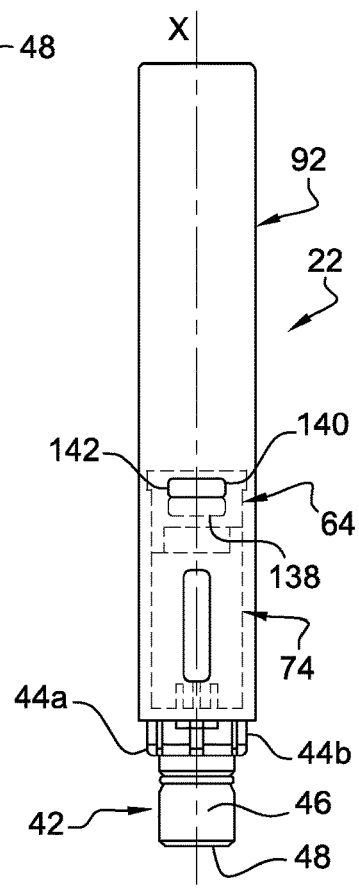

In this embodiment, the piston control member 64 is equipped with visual indication means 138 and 140 to indicate the end of the injection stroke (shown on FIGS. 20 and 21). These indication means 138, 140 comprise two indications 138, 140 printed on the piston control member 64. These printed indications 138, 140 can be seen when they are positioned opposite a window 142 formed through the outer casing 92. A first indication 138 indicates the end of the injection stroke. It can be seen during the retraction triggering step. The second indication 140 indicates the end of the operation of the automatic injection device 22. It can be seen after the step of retracting the injection needle 28.

The invention is not limited to the embodiments described and other embodiments will be clearly apparent to those skilled in the art. In particular, the disengagement member can be positioned on an element other than the outer casing and the inclination of the cam track could be deleted and compensated by a shape different from the first cam track.

The invention claimed is:

1. An automatic injection device comprising:
an injection syringe equipped with a syringe body carrying an injection needle and a piston rod mounted movably in this syringe body to cover an injection stroke whose limit is defined by an abutment of the piston rod in the syringe body,
a piston control member movable between a configuration in which it is engaged with the piston rod to push the piston rod, and a configuration in which it is disengaged from the piston rod,
a mechanism for moving the piston control member with respect to the piston rod between its engaged and disengaged configurations,
wherein the mechanism for moving the piston control member between its engaged and disengaged configurations comprises at least one first cam track carried by a disengagement member and a cam carried by the piston control member, the disengagement member being movable with respect to the piston rod and the syringe body once the piston rod has reached the end of the injection stroke, in such a way that the piston control member continue its stroke up to its disengaged configuration driven by the first cam track carried by the disengagement member which cooperates with the cam carried by the piston control member while the disengagement member is moving.

2. The automatic injection device according to claim 1, wherein the mechanism for moving the piston control member between its engaged and disengaged configurations further comprises a second cam track carried by a positioning control member which, during the injection stroke, is immobilized axially with the syringe body, the second cam track cooperating, by relative movement during the injection stroke, with the cam carried by the piston control member.

3. The automatic injection device according to claim 2, wherein the disengagement member at least partially surrounds the positioning control member, the disengagement member and the positioning control member comprising a mechanism for immobilizing their relative rotation equipped with at least one complementary groove and a tab.

4. The automatic injection device according to claim 3, wherein the tab for immobilizing rotation is formed in the disengagement member, the first cam track defining one end of the tab.

5. The automatic injection device according to claim 2, comprising first and second telescopic parts whose relative displacement controls the operation of the automatic injection device, the disengagement member being the first telescopic part, which is intended to be held by a user, and the positioning control member being the second telescopic part.

6. The automatic injection device according to claim 5, wherein the disengagement member is made movable with respect to the piston rod and the syringe body once the piston rod has reached the end of the injection stroke by elastic return member acting between the first and second telescopic parts in the direction of an elongation of the automatic injection device.

7. The automatic injection device according to claim 6, wherein the elastic return member comprises a plastic spring made integrally with the second telescopic part.

8. The automatic injection device according to claim 5, comprising a releasable blocking member for blocking the first and second telescopic parts during at least part of the injection stroke.

9. The automatic injection device according to claim 8, comprising a mechanism for releasing the releasable blocking member for blocking the first and second telescopic parts carried by a thrust member attached axially to the piston control member during the injection stroke.

10. The automatic injection device according to claim 8, wherein the releasable blocking member comprises at least one retractable ratchet carried by the second telescopic part and cooperating with a notch carried by the first telescopic part.

11. The automatic injection device according to claim 9, wherein the mechanism for releasing the releasable blocking member for blocking the first and second telescopic parts comprises a ramp for retracting the retractable ratchet.

12. The automatic injection device according to claim 5, comprising a mechanism for limiting the stroke between the first and second telescopic parts.

13. The automatic injection device according to claim 12, wherein the mechanism for limiting the stroke comprises a radial projection carried by the second telescopic part cooperating with an edge of a hole formed in the first telescopic part to limit the stroke between the first and second telescopic parts during the elongation of the automatic injection device and two axial stops carried respectively by the first and second telescopic parts arranged so as to limit the stroke between the first and second telescopic parts during the shortening of the automatic injection device.

14. The automatic injection device according to claim 1, comprising a visual indication device to indicate the end of the injection stroke.

15. The automatic injection device according to claim 14, wherein the visual indication device comprises a window formed through a first telescopic part and at least one visual indicator carried by the piston control member, the visual indicator being positioned opposite the window once the piston rod has reached the end of the injection stroke.

* * * * *